(12) United States Patent
Diab

(10) Patent No.: US 6,961,598 B2
(45) Date of Patent: Nov. 1, 2005

(54) PULSE AND ACTIVE PULSE SPECTRAPHOTOMETRY

(75) Inventor: Mohamed K. Diab, Mission Viejo, CA (US)

(73) Assignee: Masimo Corporation, Irvine, CA (US)

( * ) Notice: Subject to any disclaimer, the term of this patent is extended or adjusted under 35 U.S.C. 154(b) by 293 days.

(21) Appl. No.: 10/371,968

(22) Filed: Feb. 21, 2003

(65) Prior Publication Data

US 2003/0220576 A1 Nov. 27, 2003

Related U.S. Application Data

(60) Provisional application No. 60/358,809, filed on Feb. 22, 2002.

(51) Int. Cl.$^7$ .................................................. A61B 5/00
(52) U.S. Cl. ......................... 600/310; 600/316; 600/322
(58) Field of Search ................................. 600/310, 316, 600/322, 323, 330, 335

(56) References Cited

U.S. PATENT DOCUMENTS

| | | | |
|---|---|---|---|
| 4,655,225 A | | 4/1987 | Dähne et al. |
| 4,960,128 A | | 10/1990 | Gordon et al. |
| 4,964,408 A | | 10/1990 | Hink et al. |
| 5,041,187 A | | 8/1991 | Hink et al. |
| 5,069,213 A | | 12/1991 | Polczynski |
| 5,137,023 A | * | 8/1992 | Mendelson et al. ......... 600/316 |
| 5,163,438 A | | 11/1992 | Gordon et al. |
| 5,178,142 A | | 1/1993 | Harjunmaa et al. |
| 5,337,744 A | | 8/1994 | Branigan |
| 5,372,135 A | * | 12/1994 | Mendelson et al. ......... 600/316 |
| 5,431,170 A | | 7/1995 | Mathews |
| 5,452,717 A | | 9/1995 | Branigan et al. |
| 5,482,036 A | | 1/1996 | Diab et al. |
| 5,490,505 A | | 2/1996 | Diab et al. |
| 5,494,043 A | | 2/1996 | O'Sullivan, et al. |
| 5,529,755 A | * | 6/1996 | Higashio et al. ............ 600/316 |
| 5,533,511 A | | 7/1996 | Kaspari et al. |
| 5,553,613 A | | 9/1996 | Parker |
| 5,590,649 A | | 1/1997 | Caro et al. |
| 5,632,272 A | | 5/1997 | Diab et al. |
| 5,638,816 A | | 6/1997 | Kiani-Azarbayjany et al. |
| 5,638,818 A | | 6/1997 | Diab et al. |
| 5,645,440 A | | 7/1997 | Tobler et al. |
| 5,685,299 A | | 11/1997 | Diab et al. |
| D393,830 S | | 4/1998 | Tobler et al. |
| 5,743,262 A | | 4/1998 | Lepper, Jr. et al. |
| 5,758,644 A | | 6/1998 | Diab et al. |
| 5,760,910 A | | 6/1998 | Lepper, Jr. et al. |
| 5,769,785 A | | 6/1998 | Diab et al. |
| 5,782,757 A | | 7/1998 | Diab et al. |
| 5,785,659 A | | 7/1998 | Caro et al. |

(Continued)

FOREIGN PATENT DOCUMENTS

WO     WO 98/01071     1/1998

*Primary Examiner*—Eric F. Winakur
(74) *Attorney, Agent, or Firm*—Knobbe, Martens, Olson & Bear, LLP

(57) ABSTRACT

A pulse and active pulse spectraphotometry system comprises a light source adapted to illuminate a tissue site with optical radiation having a plurality of wavelengths selected from at least one of a primary band and a secondary band. The tissue site has a modulated blood volume resulting from the pulsatile nature of arterial blood or from an induced pulse. A detector is configured to receive the optical radiation attenuated by the tissue site and to generate a detector output responsive to absorption of the optical radiation within the tissue site. A normalizer operating on the detector output generates a plurality of normalized plethysmographs corresponding to the plurality of wavelengths. Further, a processor is configured to calculate a ratio of fractional volumes of analytes in the blood volume based upon the normalized plethysmographs.

21 Claims, 6 Drawing Sheets

U.S. PATENT DOCUMENTS

| | | | |
|---|---|---|---|
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,026,314 A | 2/2000 | Amerov et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,236,872 B1 | 5/2001 | Diab et al. |
| 6,256,623 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,334,065 B1 | 12/2001 | Al-Ali et al. |
| 6,349,228 B1 | 2/2002 | Kiani et al. |
| 6,360,114 B1 | 3/2002 | Diab et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,515,273 B2 | 2/2003 | Al-Ali |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Diab et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,725,075 B2 | 4/2004 | Al-Ali |
| 6,745,060 B2 | 6/2004 | Diab et al. |
| 6,760,607 B2 | 7/2004 | Al-All |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |

\* cited by examiner

PULSE AND ACTIVE PULSE SPECTRAPHOTOMETRY

REFERENCE TO RELATED APPLICATION

The present application claims priority benefit under 35 U.S.C. §119(e) from U.S. Provisional Application No. 60/358,809, filed Feb. 22, 2002, entitled "Pulse and Active Pulse Spectraphotometry," which is incorporated herein by reference.

BACKGROUND OF THE INVENTION

Various spectral photometric techniques have been developed for the noninvasive monitoring of blood constituent concentrations. In such systems, light of multiple wavelengths is used to illuminate a thin tissue portion of a person, such as a fingertip or earlobe. A spectrum analysis of light transmitted through or reflected from the tissue portion is used to measure the light absorption characteristics of blood flowing through the tissue portion. Utilizing calibration data, the concentration of various blood constituents is then derived from known light absorption characteristics of these blood constituents. In one spectral photometric methodology, the absolute optical spectrum of light received from the tissue portion is measured. In a differential spectral photometric methodology, blood constituent concentrations are derived from photoplethysmograph data that is responsive to blood volume changes. Pulse oximetry systems, which use the latter methodology to monitor hemoglobin constituents, have been particularly successful in becoming the standard of care for patient oxygen saturation monitoring.

SUMMARY OF THE INVENTION

Spectraphotometry for the noninvasive monitoring of blood constituents, such as blood glucose and total hemoglobin, to name a few, is highly desirable. For example, current methods for accurately measuring blood glucose involve drawing blood from the subject, which can be onerous for diabetics who must take frequent samples to closely monitor blood glucose levels. Spectraphotometry is described under no scattering conditions by the Beer-Lambert law, which states that the concentration $c_i$ of an absorbant in solution can be determined by the intensity of light transmitted through the solution, knowing the pathlength $d_\lambda$, the intensity of the incident light $I_{0,\lambda}$, and the extinction coefficient $\epsilon_{i,\lambda}$ at a particular wavelength $\lambda$. The generalized Beer-Lambert law is expressed as $$I_\lambda = I_{0,\lambda} e^{-d_\lambda \cdot \mu_{a,\lambda}} \quad (1)$$

$$\mu_{a,\lambda} = \sum_{i=1}^{n} \epsilon_{i,\lambda} \cdot c_i \quad (2)$$

where $\mu_{a,\lambda}$ is the bulk absorption coefficient and represents the probability of absorption per unit length. Dividing both sides of EQ. 1 by $I_{0,\lambda}$ and taking the logarithm yields $$\ln\left(\frac{I_\lambda}{I_{0,\lambda}}\right) = -d_\lambda \cdot \mu_{a,\lambda} \quad (3)$$

For n wavelengths, EQS. 2 and 3 can be expressed as $$\begin{bmatrix} \ln\left(\frac{I_{\lambda_1}}{I_{0,\lambda_1}}\right) \\ \vdots \\ \ln\left(\frac{I_{\lambda_n}}{I_{0,\lambda_n}}\right) \end{bmatrix} = -d \begin{bmatrix} \epsilon_{1,\lambda_1} & \cdots & \epsilon_{n,\lambda_1} \\ \vdots & \ddots & \vdots \\ \epsilon_{1,\lambda_n} & \cdots & \epsilon_{n,\lambda_n} \end{bmatrix} \begin{bmatrix} c_1 \\ \vdots \\ c_n \end{bmatrix} \quad (4)$$

assuming the pathlength is approximately constant at the wavelengths of interest, i.e. $d_{\lambda_1} = d_{\lambda_1} = \ldots d_{\lambda_n} = d$. EQ. 4 can be rewritten as $$I(\lambda) = -dA(\lambda)C \quad (5)$$

Solving for the constituent concentrations yields $$C = -\frac{1}{d} A(\lambda)^{-1} I(\lambda) \quad (6)$$

As is well known in the art, a system of linear equations can be solved if there are as many linearly independent equations as unknowns. Applied to EQ. 6, the concentration of a particular blood constituent can be calculated if the number of discrete wavelengths used is equal to the number of significant absorbers that are present and if the absorption characteristics of the significant absorbers are distinguishable at these wavelengths.

FIG. 1 is a hemoglobin extinction graph 100 illustrating the application of the Beer-Lambert law to pulse oximetry. The extinction graph 100 has an extinction coefficient axis 101 in units of $cm^{-1}$/mole and a wavelength axis 102 in units of nm. An Hb curve 110 and an $HbO_2$ curve 160 show the light absorption (extinction) properties of reduced hemoglobin and oxyhemoglobin, respectively. In particular, Hb and $HbO_2$ have significantly different absorption characteristics in the red to near IR wavelengths. Indeed, Hb absorption 110 is greater than $HbO_2$ absorption 160 in the red spectrum and, conversely, $HbO_2$ absorption 160 is greater than Hb absorption 110 in the near IR spectrum. At red and near IR wavelengths below 970 nm, where water has a significant peak, hemoglobin species are the only significant absorbers. Further, Hb and $HbO_2$ normally are the only hemoglobin species having significant concentrations in blood. Thus, only two wavelengths are needed to resolve the concentrations of Hb and $HbO_2$. Further, if one red wavelength and one IR wavelength are used, the absorption characteristics of Hb and $HbO_2$ are different enough at these wavelengths to resolve the concentrations of Hb and $HbO_2$. Typically, a pulse oximetry sensor utilizes a red emitter, such as a light emitting diode (LED) operating at 660 nm, and an IR emitter, such as a LED operating at 905 nm. As a practical matter, pulse oximetry does not explicitly compute a solution to EQ. 6, but computes a ratio of concentrations so that the pathlength, d, may be cancelled, as described with respect to EQ. 7, below.

FIG. 2 is an absorption chart 200 illustrating the absorption properties of various tissue site components. The absorption chart 200 has a total absorption axis 201 and a time axis 202. Total absorption 201 is attributed to time-invariant absorption layers 210 and a time-variant absorption layer 260. The time-invariant absorption layers 210 include a tissue absorption layer 220, which includes skin, muscle, bone, fat and pigment; a venous blood absorption layer 230; and a baseline arterial blood absorption layer 240. The time-variant absorption layer 260 is due to the pulse-added volume of arterial blood, i.e. the differential volume of arterial blood due to the inflow during systole and the outflow during diastole. The time-variant absorption layer 240 has a plethysmograph absorption profile 270.

Pulse oximetry relies on the pulsatile nature of arterial blood to differentiate blood constituent absorption from absorption of other constituents in the surrounding tissues. That is, the sensor signal generated by the pulse-added arterial blood layer 260 is isolated from the signal generated by other layers 210, including tissue, venous blood and baseline arterial blood. To do this, pulse spectraphotometry computes a ratio of the AC portion of the detected signal, which is due to the time-variant layer 260, with respect to the DC portion of the detected signal, which is due to the time-invariant layers 210, for each of multiple wavelengths. Computations of AC/DC ratios provide relative absorption measures that compensate for variations in both incident light intensity and background absorption and, hence, are responsive only to the hemoglobin in the arterial blood. As an example, pulse oximetry typically computes a red (RD) AC/DC ratio and an IR AC/DC ratio. Then, a ratio of ratios is computed, i.e.

$$RD/IR = (AC_{RD}/DC_{RD})/(AC_{IR}/DC_{IR}) \tag{7}$$

The desired oxygen saturation measurement is then computed empirically from this RD/IR ratio.

In general, pulse spectraphotometry uses multiple wavelength absorption measures, where the number and value of the wavelengths are based on the number of significant absorbers (analytes) and the absorption characteristics of these analytes. Further, pulse spectraphotometry exploits the plethysmograph absorption profile of arterial blood to cancel the time-invariant absorption contributions from other tissue components and normalization to account for variations in incident light at the different wavelengths. In particular, pulse oximetry systems are generally recognized as providing an accurate measurement of blood oxygen through a comparative measurement of oxyhemoglobin and reduced hemoglobin constituents. The application of pulse spectraphotometry to the accurate measurement of other blood constituents, such as glucose concentration or total hemoglobin, however, poses a number of difficulties, as described below.

FIG. 3 illustrates is an absorption graph 300 for water in the near infrared (IR) spectrum. The absorption graph 300 has an absorption coefficient axis 301 in units of $cm^{-1}$ and a wavelength axis 302 in units of nm. Biological tissues contain a significant percentage of water. Thus, the combination of the light absorption and scattering characteristics of water largely determine the useful range of wavelengths for pulse spectraphotometry. A water absorption curve 310 shows that water absorption increases rapidly with increasing wavelength 302 in the near IR, i.e. in the 750 nm to 3000 nm wavelength range. Fortunately for pulse oximetry, water is not a significant absorber compared with hemoglobin in the red and small wavelength portion of the near infrared, i.e. in the 660 to 940 nm wavelength range. Water, however, is a significant absorber in the larger wavelength portion of the near infrared and beyond. In particular, the penetration depth in water of wavelengths around about 1400 nm is 1 mm or less, and the penetration depth decreases rapidly with increasing wavelength beyond 1400 nm.

Some of the blood constituents of interest are not significant absorbers in the range of wavelengths where photons can penetrate biological tissue. For example, glucose is not a significant absorber in the visible spectrum. Glucose does have strong absorption bands in the far IR, having an absorption peak at 9700 nm, but photon penetration depth at that wavelength is on the order of 10 $\mu$m, i.e. around three orders of magnitude less than in the visible and near IR bands used in pulse oximetry.

When very little analyte is present, such as for blood glucose, the resulting low signal-to-noise ratio (SNR) represents an inherent system limitation for pulse spectraphotometry in the near IR. Further, there are multiple blood constituents, such as hemoglobin, cholesterol and various proteins, such as albumin and gammaglobulins that are significant absorbers in the near IR. Thus, unlike pulse oximetry, more than two wavelengths are required to resolve a particular analyte at these wavelengths.

One aspect of a pulse spectraphotometry system is a light source adapted to illuminate a tissue site with optical radiation having a plurality of wavelengths selected from at least one of a primary band and a secondary band, where the tissue site has a modulated blood volume. A detector is configured to receive the optical radiation attenuated by the tissue site and to generate a detector output responsive to absorption of the optical radiation within the tissue site. A normalizer operating on the detector output generates a plurality of normalized plethysmographs corresponding to the plurality of wavelengths. Further, a processor is configured to calculate a ratio of fractional volumes of analytes in the blood volume based upon the normalized plethysmographs. In a preferred embodiment, the primary band is in a range of about 1620 nm to about 1730 nm and the secondary band is in a range of about 1000 nm to about 1380 nm. In a more preferred embodiment, the primary band is in a range of about 1620 nm to about 1670 nm. In a most preferred embodiment, at least one of the wavelengths is selected in a range of about 1650 nm±5 nm, in a range of about 1032 nm±5 nm, in a range of about 1097 nm±5 nm or in a range of about 1375 nm±5 nm.

Another aspect of a pulse spectraphotometry system is a pulse spectraphotometry method comprising the steps of illuminating a tissue site having a pulsatile blood flow with a narrowband optical radiation, time division multiplexing the optical radiation over a plurality of wavelengths and selecting at least a portion of the wavelengths within a range of about 1620 nm to about 1730 nm. Further steps include detecting an attenuated optical radiation from the tissue site as the result of the illuminating step and calculating a ratio of analytes in the blood flow based upon the attenuated optical radiation. In a preferred embodiment, the selecting step comprises the substep of selecting at least one wavelength in a range of about 1620 nm to about 1670 nm. In a more preferred embodiment, the selecting step comprises a substep of selecting at least one wavelength in a range of about 1650 nm±5 nm. In another preferred embodiment, the pulse spectraphotometry method comprises the further step of selecting a second portion of the wavelengths within a range of about 1000 nm to about 1380 nm. In another more preferred embodiment, the selecting a second portion step comprises a substep of selecting at least one wavelength in a range of about 1032 nm±5 nm, in a range of about 1097 nm±5 nm or in a range of about 1375 nm±5 nm.

Yet another aspect of a pulse spectraphotometry system is an optical radiation means for illuminating a tissue site and a filter means for determining a nominal wavelength of the optical radiation, where the nominal wavelength is selected from a range of about 1620 nm to about 1730 nm. The pulse spectraphotometry system also has a detector means for receiving the optical radiation after transmission through or reflection from the tissue site and for generating a corresponding plethysmograph signal and a processor means for calculating a ratio of analyte portions of pulsatile blood flow within the tissue site based upon the plethysmograph signal. In a preferred embodiment, the nominal wavelength is selected from a range of about 1620 nm to about 1670 nm. In a more preferred embodiment, the nominal wavelength is selected from a range of about 1650 nm±5 nm. In another preferred embodiment, the nominal wavelength is selected from a range of about 1000 nm to about 1380 nm. In another more preferred embodiment, the nominal wavelength is selected from a range of about 1032 nm±5 nm, a range of about 1097 nm±5 nm, or a range of about 1375 nm±5 nm. In yet another preferred embodiment, the nominal wavelength is selected from a range of about 2000 nm to about 2500 nm.

DETAILED DESCRIPTION OF THE PREFERRED EMBODIMENT

Figure 4:
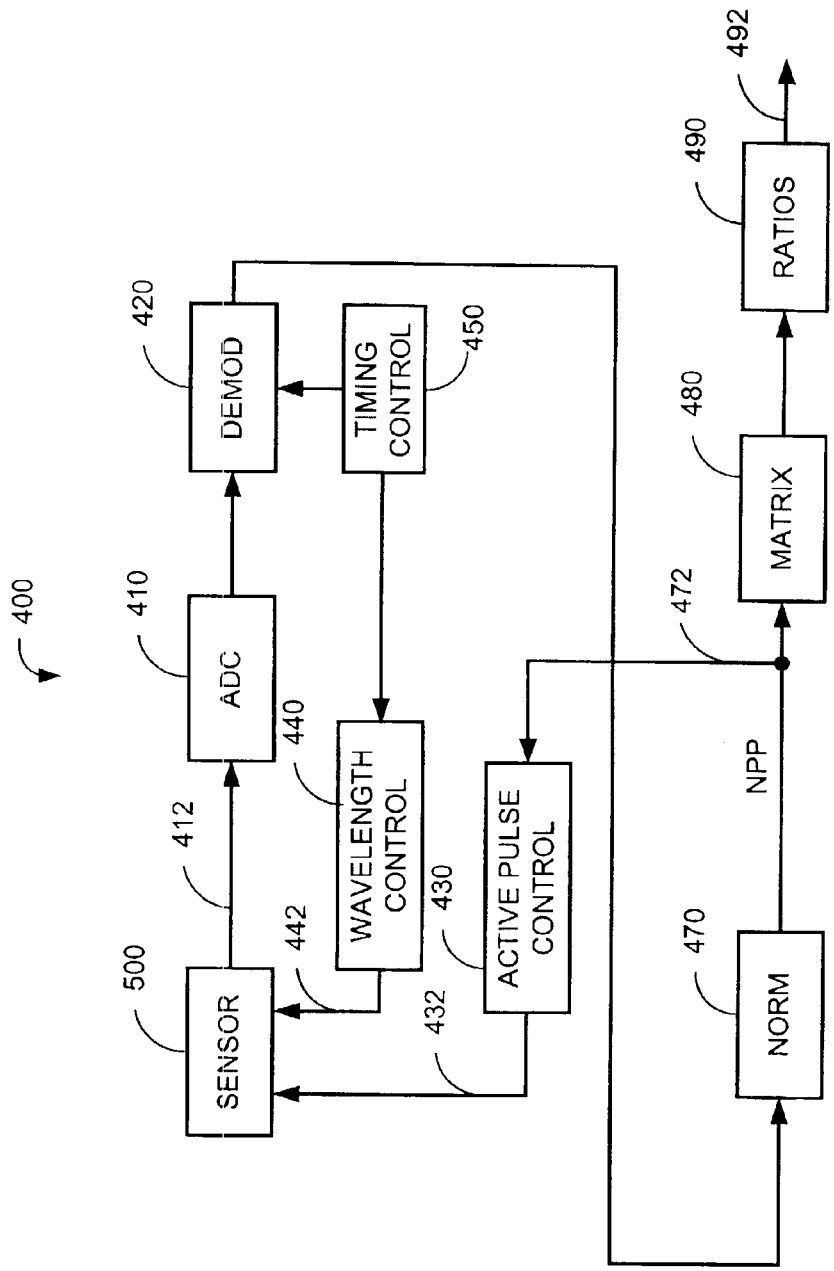
FIG. 4 is a functional block diagram of a pulse spectraphotometry system.
Figure 5:
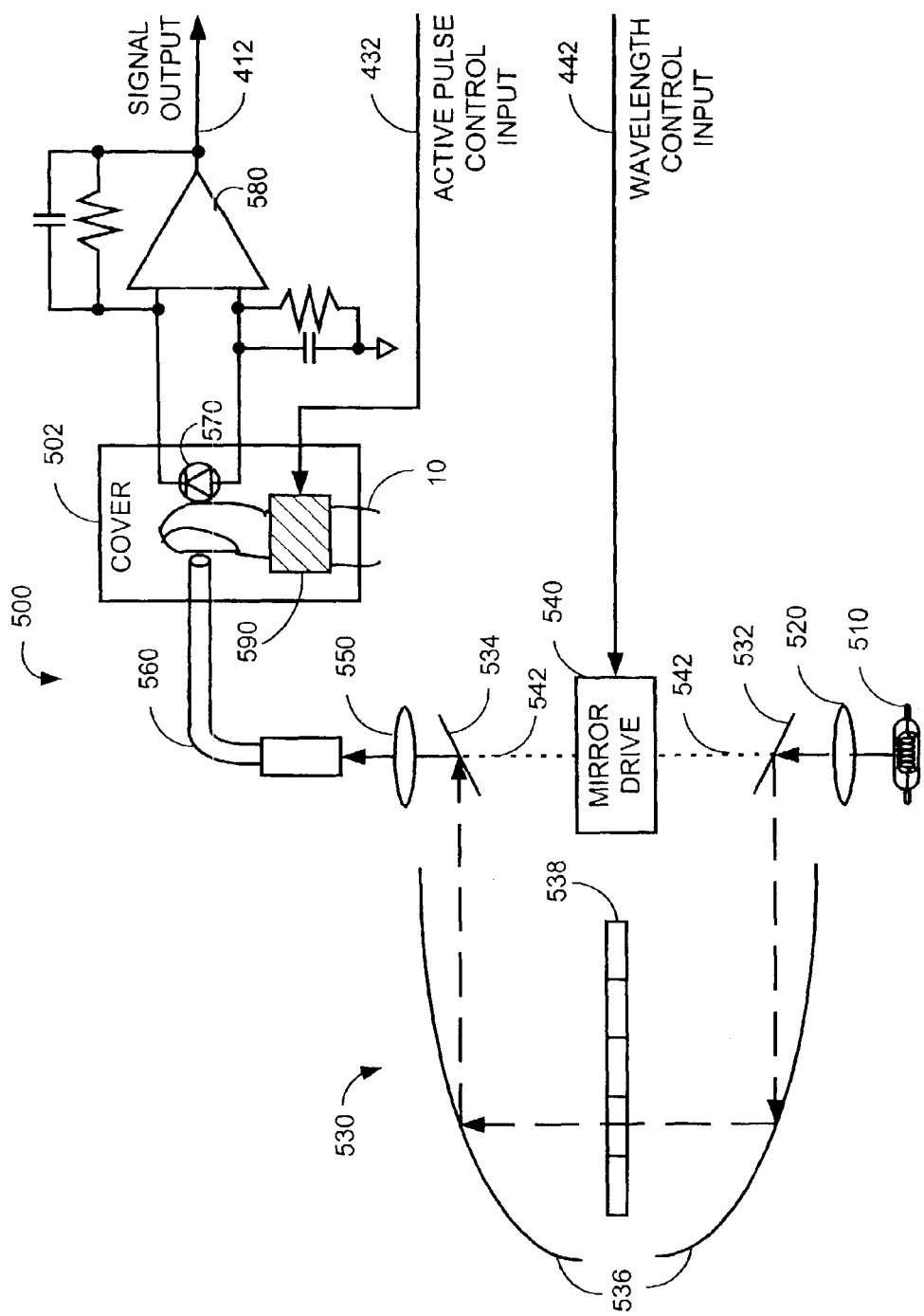
FIG. 5 is a functional block diagram of a physiological sensor for pulse spectraphotometry.

FIG. 4 illustrates a pulse spectraphotometry system having a signal processor 400 and a sensor 500. Herein, the term pulse spectraphotometry is intended to include spectrophotometry based upon the pulsatile characteristics of arterial blood, as described above, and spectraphotometry based upon an active pulse, as described below. The sensor 500 is described in detail with respect to FIG. 5, below. The signal processor 400 has an analog-to-digital converter (ADC) 410, a demodulator 420, an active pulse control 430, a wavelength control 440, a timing control 450, a normalizer 460, a matrix calculator 480 and a ratio calculator 490. The sensor 500 illuminates a tissue site 10 (FIG. 5) with multiple wavelengths, one at a time, and generates a signal output 412 that is responsive to the intensity of optical radiation absorbed by the tissue site 10 (FIG. 5). The signal output 412 is a time division multiplexed (TDM) signal with multiple time slots corresponding to the multiple wavelengths. The timing control 450 determines the time slots. The ADC 410 digitizes the signal output 412, and the demodulator 420 separates the individual time slots and corresponding responses. The demodulator output 422 is then normalized 470, such as by dividing the AC by the DC, as described above, to generate a normalized photoplethysmograph (NPP) 472.

Taking into account scattering in the tissue media and the resulting wavelength dependent optical pathlengths, the transmitted intensity through the media and, hence, the sensor signal output 412 can be approximated as $$I_\lambda \approx A_\lambda e^{-mpl_\lambda \cdot \mu_{a,\lambda}} \tag{8}$$

which is similar in form to EQ. 1, described above, where $A_\lambda$ is a function of the incident light, the geometry of the tissue media and the tissue media composition; $mpl_\lambda$ is the wavelength dependent mean pathlength; and $\mu_{a,\lambda}$ is the bulk absorption coefficient expressed in EQ. 2, above. The NPP 472 can be derived from EQ. 8 as follows $$dI_\lambda = -mpl_\lambda \cdot A_\lambda e^{-mpl_\lambda \cdot \mu_{a,\lambda}} \cdot d\mu_{a,\lambda} \tag{9}$$

$$NPP = \frac{AC_\lambda}{DC_\lambda} = \frac{dI_\lambda}{I_\lambda} = -mpl_\lambda \cdot d\mu_{a,\lambda} \tag{10}$$

Assume $$d\mu_{a,\lambda} \approx \mu_{ab_\lambda} \cdot \Delta V/V \tag{11}$$

where $\mu_{ab_\lambda}$ is the bulk absorption coefficient of the blood, V is the tissue volume and $\Delta V$ is the change in tissue volume due to the pulsatile blood flow. EQ. 10 can then be written as $$NPP = -mpl_\lambda \cdot \mu_{a,b_\lambda} \cdot v_b \tag{12}$$

$$\mu_{ab_\lambda} = \sum_i v_i \cdot \mu_i; \quad \sum_i v_i = 1 \tag{13}$$

which is similar in form to EQS. 2 and 3, described above, where $v_b = \Delta V/V$ is the fractional blood volume. Also, $v_i$ is the fractional volume in the blood of the ith analyte and $\mu_i$ is the absorption coefficient of the ith analyte. For n wavelengths, EQS. 12 and 13 can be expressed as $$\begin{bmatrix} NPP_1 \\ \vdots \\ NPP_n \end{bmatrix} = -\begin{bmatrix} mpl_{\lambda_1} & \cdots & 0 \\ \vdots & \ddots & \vdots \\ 0 & \cdots & mpl_{\lambda_n} \end{bmatrix} \begin{bmatrix} \mu_{1,\lambda_1} & \cdots & \mu_{n,\lambda_1} \\ \vdots & \ddots & \vdots \\ \mu_{1,\lambda_n} & \cdots & \mu_{n,\lambda_n} \end{bmatrix} \begin{bmatrix} v_1 \\ \vdots \\ v_n \end{bmatrix} v_b \tag{14}$$

EQ. 14 can be rewritten as $$NPP = -MPL(\lambda)\mu(\lambda)Vv_b \tag{15}$$

Solving for the analyte fractional volumes yields $$V = -[MPL(\lambda)\mu(\lambda)]^{-1}NPP/v_b \tag{16}$$

which is similar in form to EQ. 6. The matrix calculator 480 performs the matrix inversion indicated in EQ. 16. The ratio calculator 490 is then used to cancel $v_b$ and determine a desired ratio of fractional volumes of analytes in the blood. The mean pathlengths can be determined by calibration or separate measurements. A pathlength measurement method is described in U.S. patent application Ser. No. 09/925,982 entitled "Optical Spectroscopy Pathlength Measurement System," incorporated by reference herein. In particular, using the sensor 500 and the wavelengths described in detail with respect to FIG. 6, below, the ratio calculator output 492 advantageously provides the ratio of the fractional volume of blood glucose to the fractional volume of water in the blood, which is desired for diabetes diagnosis and monitoring.

Figure 1:
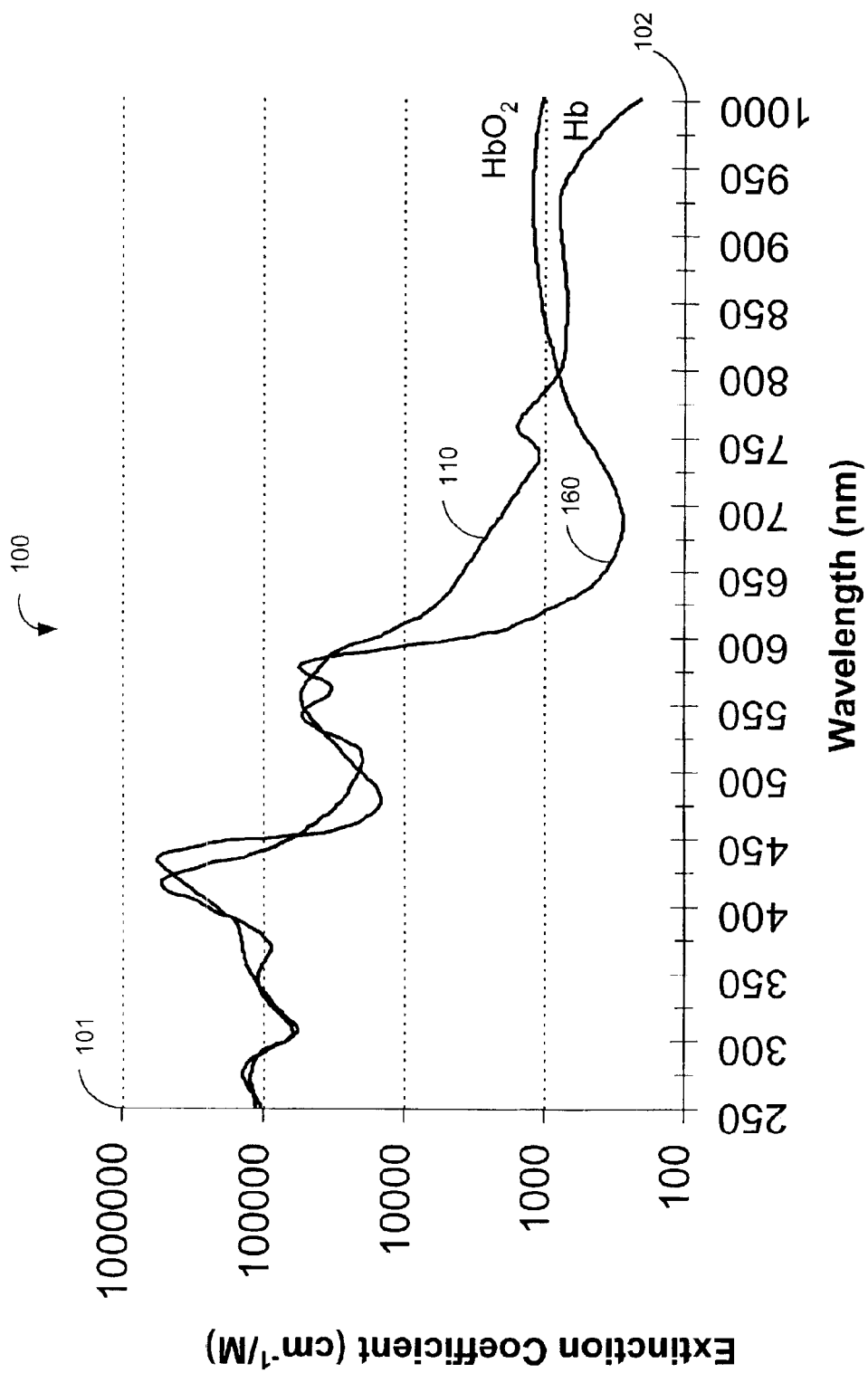
FIG. 1 is a graph of oxyhemoglobin and reduced hemoglobin extinction coefficients versus wavelength.
Figure 2:
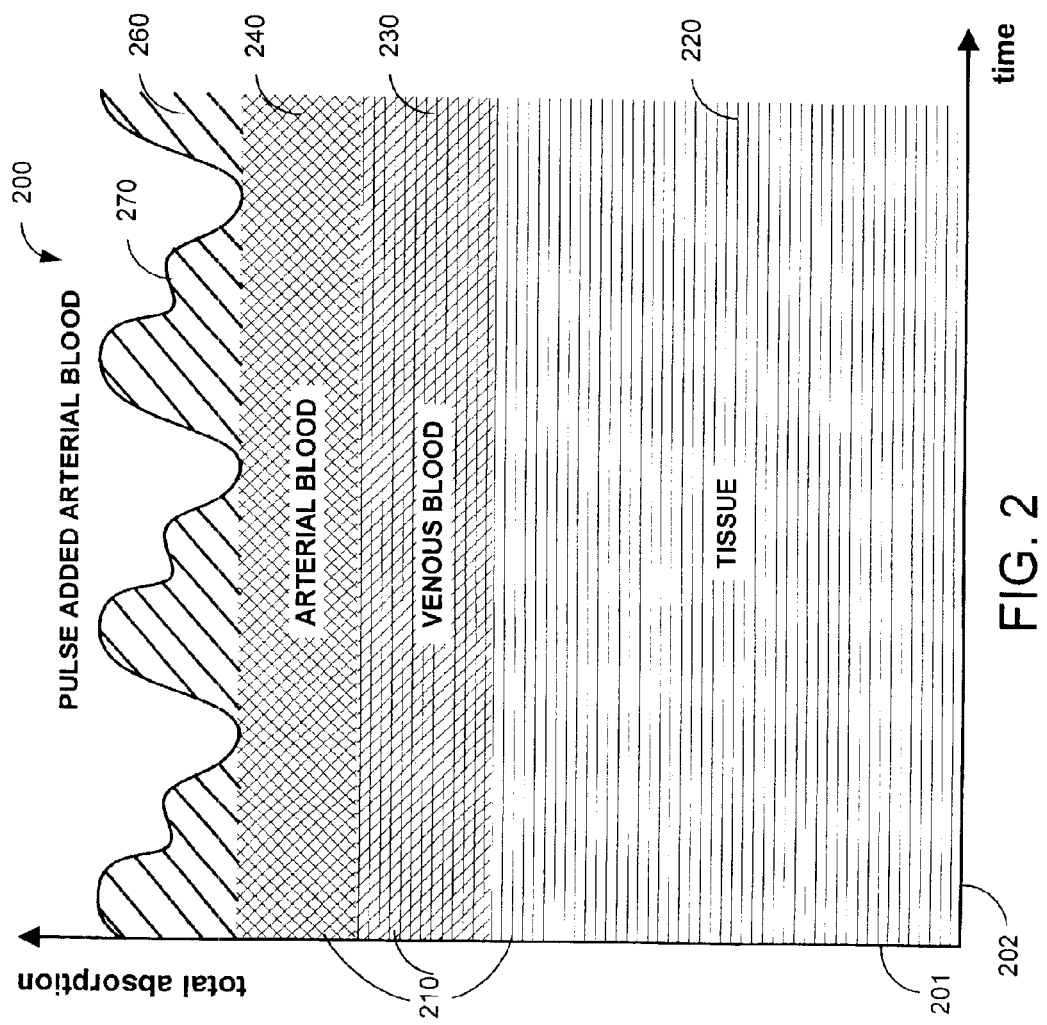
FIG. 2 is a graph of total tissue and blood light absorption versus time.
Figure 3:
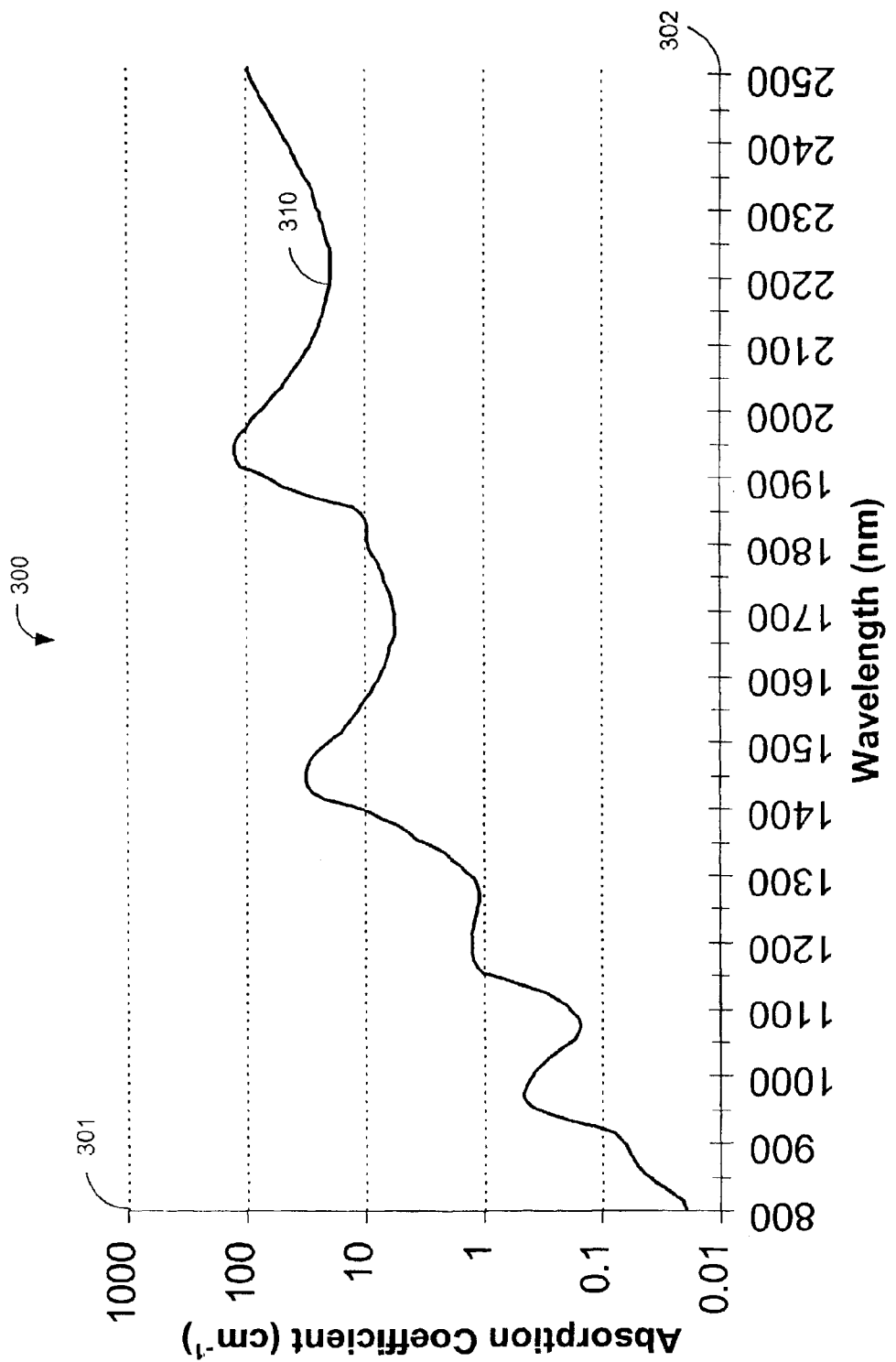
FIG. 3 is a graph of water absorption versus wavelength across a portion of the near infrared spectrum.

Also shown in FIG. 4, an active pulse control 430 provides an active pulse control input to the sensor 500. Advantageously, an active pulse mechanism induces a periodic change in the flow of blood through a tissue medium, which can provide a larger AC signal, as described with respect to FIG. 2, above, and a greater SNR as a result. The degree of blood flow modulation is determined by feedback from the NPP 472 so as to control the AC signal level. The active pulse mechanism is described in further detail with respect to FIG. 5, below.

Further shown in FIG. 4, a wavelength control 440 provides a wavelength control input 442 to the sensor 500.

The wavelength control 440 receives input from the timing control 450 and, accordingly, determines the wavelength sequence of optical radiation illuminating the tissue site 10 (FIG. 5) in a manner analogous to the LED drive signals transmitted from a pulse oximetry monitor to a pulse oximetry sensor, which is well-known in the art. The sensor wavelength control is described in further detail with respect to FIG. 5, below.

FIG. 5 illustrates a pulse spectraphotometry sensor 500 having an ambient light cover 502, a light source 510, a condensor lens 520, a narrow-band, multiple-wavelength filter 530, a mirror drive 540, a collecting lens 550, a fiberoptic cable 560, a detector 570, an amplifier 580 and an active pulse transducer 590. The light source 510 and condensor lens 520 provide broadband optical radiation to the wavelength filter 530, which passes selected, narrow-band portions of the optical radiation to the collecting lens 550. The narrowband optical radiation is coupled to the fiberoptic cable 560, which transmits the narrowband optical radiation to illuminate a tissue site 10 that is shielded from ambient light by the cover 502. The detector 570 generates a current proportional to the intensity of attenuated optical radiation received after transmission through or reflection from the illuminated tissue site 10. The received intensity is responsive to the absorption coefficients of blood constituents, as described with respect to EQS. 8–13, above. An amplifier 580 provides a gain in the detector current and generates a signal output 412 to the processor 400 (FIG. 4), described above.

As shown in FIG. 5, the wavelength filter 530 has an input mirror 532, an output mirror 534, a parabolic mirror 536 and an optical filter array 538. The input mirror 532 and output mirror 534 are rotatable according to drive signals 542 from the mirror drive 540. As such, the mirror drive 540 controls the optical path of light around the parabolic mirror 536 and through a particular optical filter in the optical filter array 538. Each optical filter in the optical filter array 538 is manufactured to a different narrow passband. Thus, the wavelength filter 530 determines the nominal wavelength of optical radiation that illuminates the tissue site 10 at any particular time. The wavelength control input 442 from the signal processor 400 (FIG. 4) synchronizes the timing of the input mirror 532 and output mirror 534 rotations and, accordingly, the tissue illumination wavelength and the characteristics of the TDM signal output 412, described with respect to FIG. 4, above.

Also shown in FIG. 5 is the active pulse transducer 590, which modulates the blood flow at the tissue site 10 according to the active pulse control input 432, described with respect to FIG. 4, above. In one embodiment, the active pulse transducer is a pressure device applied to a patient's digit. The pressure device may be, for example, a cuff having a bladder that periodically fills and empties with a gas or liquid, such as air or water. Although shown separate from the sensor in FIG. 5, the transducer 590 may be an integral part of the sensor. Active pulse apparatuses and methods are described in U.S. Pat. No. 6,151,516 entitled "Active Pulse Blood Constituent Monitoring," incorporated by reference herein.

In one sensor embodiment, the light source 510 is a high intensity incandescent lamp such that several mw of power is introduced into a tissue site, e.g. a finger, at each wavelength. The filter array 538 utilizes multiple Fabry-Perot optical interference filters each having a 10 nm bandwidth. The detector is a InGaAs photodiode having a 2 mm–3 mm diameter, a useful response bandwidth in the range of 850 nm to 1700 nm and the highest possible intrinsic shunt resistance. The amplifier is a transimpedance amplifier such as Analog Devices 743, having a feedback resistance in the range of 20 to 40 MΩ. The TDM signal output 412 (FIG. 4) switches wavelengths at a 40 Hz rate.

Figure 6:
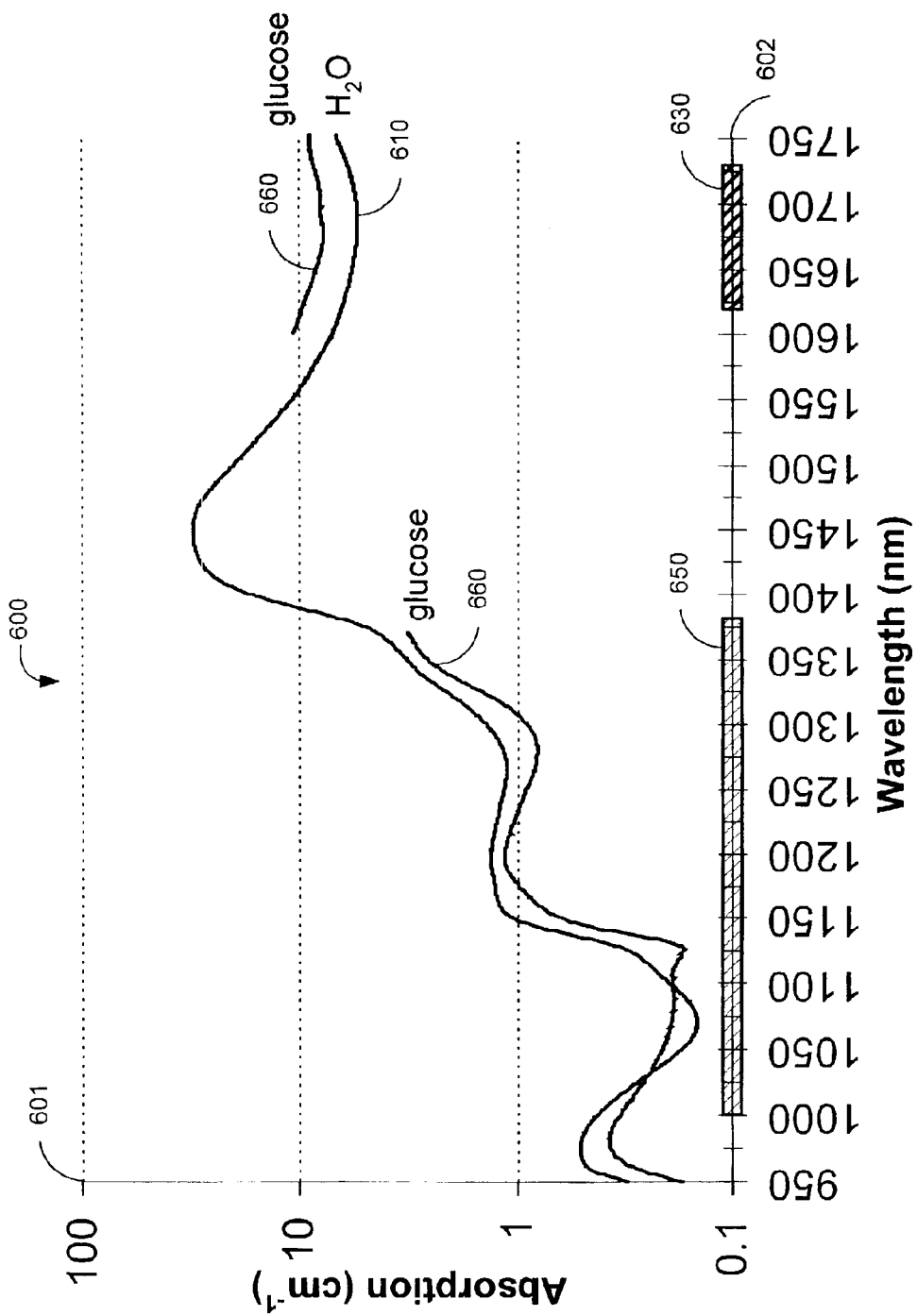
FIG. 6 is a graph of water and glucose absorption versus wavelength including critical wavelength portions of the near infrared spectrum for pulse spectraphotometry.

FIG. 6 is a graph 600 having a logarithmic absorption axis 601 in units of $cm^{-1}$ versus a linear wavelength axis 602 in units of nm. Plotted on the graph 600 is a water absorption curve 610 and glucose absorption curve 660. In a preferred embodiment, the pulse spectraphotometry system is adapted to operate in a primary wavelength band 630 having a range of about 1620 nm to about 1730 nm. In a more preferred embodiment, the pulse spectraphotometry system is adapted to operate in a sub-band of the primary band 630 having a range of about 1620 nm to about 1670 nm. In a most preferred embodiment, the pulse spectraphotometry system is adapted to operate at a nominal wavelength of about 1650 nm±5 nm.

In a preferred embodiment, the pulse spectraphotometry system may also be adapted to operate in a secondary wavelength band 650 having a range of about 1000 nm to about 1380 nm. In a more preferred embodiment, the pulse spectraphotometry system may also adapted to operate at a nominal wavelength around about 1032 nm±5 nm and/or 1097 nm±5 nm, where water and glucose are isobestic. The pulse spectraphotometry system may also be adapted to operate at a nominal wavelength around about 1375 nm±5 nm where water has about the same absorption as in the primary wavelength band. Although the wavelength bands of about 1620 nm to about 1730 nm and of about 1000 nm to about 1380 nm are denoted above as primary and secondary wavelength bands, respectively, the pulse spectraphotometry system may operate solely within the primary wavelength band, solely within the secondary wavelength band or concurrently within both bands.

As shown in FIG. 6, the preferred embodiment encompasses a critical range of wavelengths for a pulse spectraphotometry system, as described herein. Water absorption rapidly increases an order of magnitude between 1300 nm and 1400 nm and two orders of magnitude between 1300 nm and 1900 nm. Water accounts for a significant percentage of blood, interstitial fluids and other tissue. Further, the intensity of optical radiation transmitted through tissue decreases exponentially with absorption, as described with respect to EQ. 1, above. Accordingly, for the same input intensity, the detected output intensity, i.e. the DC output of the detector 570 (FIG. 5), is roughly 200 times less at 1400 nm as compared to 1300 nm. The result is that the signal drops below the electronic noise present in the photodiode and preamp at wavelengths much above 1300 nm. There is a small range of wavelengths in the primary band 630, which encompasses the preferred range of wavelengths, where it is very difficult, but advantageous, to operate the pulse spectraphotometry system. Within this range, water absorption drops to a value roughly equal to its value around 1380 nm, and it is possible to obtain a working plethysmograph, but only by minimizing all noise sources, including the elimination of ambient light; the selection of low noise electronic components, such as described with respect to FIG. 5, above; and careful component layout and interconnection to avoid noise sources such as crosstalk and ground noise, as is well-known in the art.

There are several advantages of the primary band 630 of wavelengths for the spectraphotometric determination of certain blood constituents. At least five blood constituents of significance are in the near IR, including water, glucose, hemoglobin, urea and protein. In one embodiment, the pulse spectraphotometry system operates over at least five wavelengths for resolution of these analytes. The absorption characteristics of these analytes must be sufficiently different at the operating wavelengths to insure a robust solution, as determined by the condition number of the resulting matrix, as is well known in the art. Operating within the primary band 630 and the secondary band 650 increases the variation in absorption characteristics. In particular, there is a crossover of water absorption and glucose absorption between 1380 nm and 1620 nm, which allows glucose to be more easily distinguished from water.

Another significant advantage of the primary band 630 is that glucose absorption is an order of magnitude larger within that band than for the secondary band 650, i.e. at wavelengths below 1380 nm. Because intensity varies exponentially with absorption, as described with respect to EQ. 1, measurements derived from the primary band 630 are significantly more sensitive to variations in blood glucose than those derived from the secondary band 650.

Yet another advantage to the primary band 630 is that, due to the higher absorption of at least some blood constituents in the primary band, including water and glucose, the plethysmograph signal is larger in magnitude in the primary band 630 than for the secondary band 650. Although the SNR of the plethysmograph signal is lower in the primary band 630, the larger absolute magnitude provides a greater dynamic range for blood constituent measurements.

Although a primary band 630 and secondary band 650 are described above with respect to a sensor 500 (FIG. 5) configured to transmit light through a tissue site 10 (FIG. 5), in another embodiment, the sensor 500 (FIG. 5) may be configured to detect illumination reflected from a tissue site 10 (FIG. 5). Because such a reflectance sensor suffers less tissue absorption than a transmission sensor, the primary band 630 may be somewhat broader, in the range of about 1575 nm to 1775 nm and a tertiary band of wavelengths in the range of about 2000 nm to about 2500 nm may be utilized.

A pulse and active pulse spectraphotometry system has been disclosed in detail in connection with various embodiments. These embodiments are disclosed by way of examples only and are not to limit the scope of the claims that follow. One of ordinary skill in the art will appreciate many variations and modifications within the scope of this invention.

What is claimed is:

1. A pulse spectraphotometry system comprising:
   a light source adapted to illuminate a tissue site with optical radiation having a plurality of wavelengths selected from at least one of a primary band and a secondary band, said tissue site having a modulated blood volume;
   a detector configured to receive said optical radiation attenuated by said tissue site and to generate a detector output responsive to absorption of said optical radiation within said tissue site;
   a normalizer operating on said detector output to generate a plurality of normalized plethysmographs corresponding to said plurality of wavelengths; and
   a processor configured to calculate a ratio of fractional volumes of analytes in said blood volume based upon said normalized plethysmographs,
   wherein said secondary band is in a range of about 1000 nm to about 1380 nm.

2. The pulse spectraphotometry system according to claim 1 wherein said primary band is in a range of about 1620 nm to about 1730 nm.

3. The pulse spectraphotometry system according to claim 2 wherein said primary band is in a range of about 1620 nm to about 1670 nm.

4. The pulse spectraphotometry system according to claim 3 wherein at least one of said wavelengths is selected in a range of about 1650 nm ±5 nm.

5. The pulse spectraphotometry system according to claim 1 wherein at least one of said wavelengths is selected in a range of about 1032 nm±5 nm.

6. The pulse spectraphotometry system according to claim 1 wherein at least one of said wavelengths is selected in a range of about 1097 nm±5 nm.

7. The pulse spectraphotometry system according to claim 1 wherein at least one of said wavelengths is selected in a range of about 1375 nm±5 nm.

8. A pulse spectraphotometry system comprising:
   a light source adapted to illuminate a tissue site with optical radiation having, a plurality of wavelengths the selected from at least one of a primary band and a secondary band, said tissue site having a modulated blood volume;
   a detector configured to receive said optical radiation attenuated by said tissue site and to generate detector output responsive to absorption of said optical radiation within said tissue site;
   a normalizer operating on said detector output to generate a plurality of normalized plethysmographs corresponding to said plurality of wavelengths; and
   a processor configured to calculate a ratio of fractional volumes of analytes in said blood volume based upon said normalized plethysmographs;
   wherein said detector is configured to receive said optical radiation after reflection from said tissue site and said wavelengths are further selected from a tertiary band of said wavelengths in a range of about 2000 nm to about 2500 nm.

9. A pulse spectraphotometry method comprising the steps of:
   illuminating a tissue site having a pulsatile blood flow with a narrowband optical radiation;
   time division multiplexing said optical radiation over a plurality of wavelengths;
   selecting at least a portion of said wavelengths within a range of about 1620 nm to about 1730 nm;
   selecting a second portion of said wavelengths within a range of about 1000 nm to about 1380 nm;
   detecting an attenuated optical radiation from said tissue site as the result of said illuminating step; and
   calculating a ratio of analytes in said blood flow based upon said attenuated optical radiation.

10. The pulse spectraphotometry method according to claim 9 wherein said selecting step comprises the substep of selecting at least one wavelength in a range of about 1620 nm to about 1670 nm.

11. The pulse spectraphotometry method according to claim 9 wherein said selecting step comprises a substep of selecting at least one wavelength in a range of about 1650 nm±5 nm.

12. The pulse spectraphotometry method according to claim 9 wherein said selecting a second portion step comprises a substep of selecting at least one wavelength in a range of about 1032 nm±5 nm.

13. The pulse spectraphotometry method according to claim 9 wherein said selecting a second portion step comprises a substep of selecting at least one wavelength in a range of about 1097 nm±5 nm.

14. The pulse spectraphotometry method according to claim 9 wherein said selecting a second portion step comprises a substep of selecting at least one wavelength in a range of about 1375 nm±5 nm.

15. A pulse spectraphotometry system comprising:
an optical radiation means for illuminating a tissue site;
a filter means for determining a nominal and secondary wavelength of said optical radiation, said nominal wavelength selected from a range of about 1620 nm to about 1730 nm or from a range of about 2000 nm to about 2500 nm, said secondary wavelength selected from a range of about 1000 nm to about 1380 nm;
a detector means for receiving said optical radiation after transmission through or reflection from said tissue site and generating a corresponding plethysmograph signal; and
a processor means for calculating a ratio of analyte portions of pulsatile blood flow within said tissue site based upon said plethysmograph signal.

16. The pulse spectraphotometry system according to claim 15 wherein said nominal wavelength is selected from a range of about 1620 nm to about 1670 nm.

17. The pulse spectraphotometry system according to claim 16 wherein said nominal wavelength is selected from a range of about 1650 nm±5 nm.

18. The pulse spectraphotometry system according to claim 15 wherein said secondary wavelength is selected from a range of about 1032 nm±5 nm.

19. The pulse spectraphotometry system according to claim 15 wherein said secondary wavelength is selected from a range of about 1097 nm±5 nm.

20. The pulse spectraphotometry system according to claim 15 wherein said secondary wavelength is selected from a range of about 1375 nm±5 nm.

21. The pulse spectraphotometry system according to claim 15 wherein said nominal wavelength is selected from a range of about 2000 nm to about 2500 nm.

* * * * *

UNITED STATES PATENT AND TRADEMARK OFFICE
CERTIFICATE OF CORRECTION

PATENT NO. : 6,961,598 B2  
APPLICATION NO. : 10/371968  
DATED : November 1, 2005  
INVENTOR(S) : Diab Page 1 of 1

It is certified that error appears in the above-identified patent and that said Letters Patent is hereby corrected as shown below:

First Page, column 1 (Assignee), line 1, after "Corporation," insert -- 40 Parker --.

At column 2, line 11, after " $d_{\lambda_1}$ " delete " $= d_{\lambda_1}$ " and insert -- $= d_{\lambda_2}$ --, therefore.

At column 6, line 17 (Approx.), delete "$\mu_{a,b\lambda}$" and insert -- $\mu_{ab\lambda}$ --, therefore.

At column 10, line 6, in Claim 4, delete "nm ±5." and insert -- nm±5. --, therefore.

At column 10, line 18, in Claim 8, delete "having," and insert -- having --, therefore.

At column 10, line 18, in Claim 8, after "wavelengths" delete "the".

At column 10, line 23, in Claim 8, after "generate" insert -- a --.

Signed and Sealed this

Nineteenth Day of June, 2007

JON W. DUDAS  
*Director of the United States Patent and Trademark Office*